United States Patent
Puthiaparampil et al.

(10) Patent No.: US 7,238,826 B2
(45) Date of Patent: *Jul. 3, 2007

(54) BORONATE ESTERS

(75) Inventors: Tom Thomas Puthiaparampil, Karnataka (IN); Sumithra Srinath, Bangalore (IN); Madhavan Sridharan, Karnataka (IN); Sambasivam Ganesh, Karnataka (IN)

(73) Assignee: Biocon Limited, Electronic, Bangalore (IN)

( * ) Notice: Subject to any disclaimer, the term of this patent is extended or adjusted under 35 U.S.C. 154(b) by 121 days.

This patent is subject to a terminal disclaimer.

(21) Appl. No.: 10/923,934

(22) Filed: Aug. 23, 2004

(65) Prior Publication Data
US 2006/0040898 A1  Feb. 23, 2006

Related U.S. Application Data

(63) Continuation-in-part of application No. 10/505,528, filed as application No. PCT/IN02/00032 on Feb. 25, 2002.

(51) Int. Cl.
*C07F 5/04* (2006.01)
(52) U.S. Cl. ..................................... 558/288
(58) Field of Classification Search ................ 558/288
See application file for complete search history.

(56) References Cited

U.S. PATENT DOCUMENTS 5,399,722 A * 3/1995 Beck et al. ............... 549/375
5,481,009 A   1/1996 Matsumoto et al.
5,998,633 A   12/1999 Jacks et al.
6,140,527 A   10/2000 Kunihiro et al.
2005/0154213 A1* 7/2005 Puthiaparampil et al. ... 549/213
2006/0040898 A1  2/2006 Puthiaparampil et al.

FOREIGN PATENT DOCUMENTS

| EP | 0 104 750 B1 | 4/1984 |
| EP | 0 319 847 B1 | 6/1989 |
| EP | 0 577 040 B1 | 1/1994 |
| EP | 0 909 757 A2 | 4/1999 |
| WO | WO-2001/72706 A1 | 10/2001 |
| WO | WO/02/057274 A1 * | 7/2002 |
| WO | WO-2003/070733 A1 | 8/2003 |

OTHER PUBLICATIONS

Frechet et al. "Use of Polymers as Protecting Groups in Organic Synthesis. Application of Polystyrylboronic Acid to the One-Pot Synthesis of Acylated Carbohydrate Derivatives" Journal of the American Chemical Society 1979 vol. 101, Iss 2, pp. 432-436.*
International Search Report, PCT/IN02/00032, Date of mailing Jun. 4, 2002.
Office Action Summary for U.S. Appl. 10/505,528, Date of mailing Oct. 4, 2006.

* cited by examiner

*Primary Examiner*—Joseph K. McKane
*Assistant Examiner*—Joseph R. Kosack
(74) *Attorney, Agent, or Firm*—Andrea L. C. Robidoux; Choate, Hall & Stewart LLP

(57) ABSTRACT

The present invention relates to optically active boronate derivatives which are useful as intermediates for the synthesis of HMG-CoA enzyme inhibitors such as atorvastatin, cerivastatin, rosuvastatin, pitavastatin, and fluvastatin.

11 Claims, No Drawings

BORONATE ESTERS

PRIORITY CLAIM

The present application is a continuation-in-part of U.S. patent application Ser. No. 10/505,528, filed Aug. 23, 2004, which claims the benefit under 35 U.S.C. § 371 of International Application Number PCT/IN02/00032 (published PCT Application Number WO 03/070733) filed on Feb. 25, 2002, the entirety of both of which is hereby incorporated herein by reference.

FIELD OF THE INVENTION

The present invention relates to optically active boronate derivatives which are useful as intermediates for the synthesis of HMG-CoA enzyme inhibitors such as atorvastatin, cerivastatin, rosuvastatin, pitavastatin, and fluvastatin.

BACKGROUND OF THE INVENTION

Esters and derivatives of formula I:

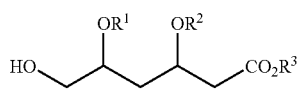

where $R^1$ and $R^2$ are independently chosen alkyl of one to three carbons and $R^3$ is alkyl of 1 to 8 carbon atoms, and alternatively compounds of formula Ia:

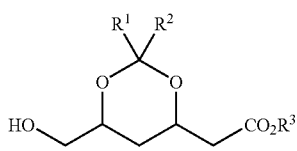

wherein $R^1$ and $R^2$ are independently chosen from alkyl of one to three carbons or phenyl, or $R^1$ and $R^2$ are taken together as $—(CH_2)_n—$ wherein n is 4 or 5, and $R^3$ is alkyl of 1 to 8 carbon atoms, are important intermediates in the preparation of compounds useful as anti-hypercholesterolemic agents having an inhibitory effect on HMG-CoA reductase. Such agents include atorvastatin, cerivastatin, pitavastatin, fluvastatin and rosuvastatin.

Compounds of formula Ib:

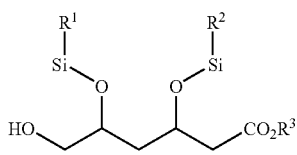

wherein $R^1$ and $R^2$ are alkyl of 1 to 5 carbons, and $R^3$ is as defined above, are also useful as intermediates in the preparation of said anti-hypercholesterolemic agents.

EP 0 319 847 describes a process for the preparation of compounds of formula I starting from L-malic acid. This process, however, suffers from the fact that the process is not industrially scalable and also possesses purification problems due to the non-crystalline nature of the intermediates.

U.S. Pat. No. 5,399,722 describes a process for preparing such compounds starting from commercially available ethyl ω-cloroacetoacetate or its benzyloxy derivative. The disadvantages of this process are that a stereo-selective reduction using a costly ruthenium-BINAP catalyst is employed and the desired compound of formula I is obtained in six steps.

U.S. Pat. No. 5,481,009 describes a five-step process for preparing such compounds starting from 4-phenyl-3-butenoic acid. The process uses both expensive materials such as N,O-dimethyl hydroxylamine and hazardous steps (ozonolysis) to obtain the desired product.

U.S. Pat. No. 5,998,633 describes a process for the preparation of protected esters of 3,4-dihydroxy butyric acid from a carbohydrate moiety which is transformed into the desired 3,4-dihydroxy butanoic acid derivatives in about 4 steps. The 3,4-dihydroxy butanoic acid derivative is then functionalized into compounds of formula I involving a multiple number of steps.

U.S. Pat. No. 6,140,527 describes a process for producing butyric acid derivatives starting from a butene derivative followed by reaction with a reagent capable of adding across the double bond. However, this procedure necessitates the need for a resolution step.

EP 0 104 750 describes a process for the preparation of 5-hydroxy-3-oxo pentanoic acid derivatives by alkylation of 3-hydroxybutyrate derivatives. The products of this process are racemic thus necessitating a resolution step.

Thus, there remains an unmet need to provide a simple and industrially scalable process for the preparation of derivatives of formula I starting from commercially available and inexpensive materials. It would be also be desirable to provide a method of preparing compounds of formula I in a stereoselective manner.

SUMMARY OF THE INVENTION

It has been found that the compounds and methods, as described herein, are useful for the preparation of anti-hypercholesterolemic agents having an inhibitory effect on HMG-CoA reductase, such as atorvastatin, cerivastatin, pitavastatin, fluvastatin and rosuvastatin.

DETAILED DESCRIPTION OF CERTAIN EMBODIMENTS OF THE INVENTION

According to one embodiment, the present invention provides a compound of formula IIa:

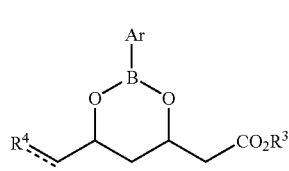

wherein:
Ar is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur;

$R^3$ is straight or branched $C_{1-8}$ alkyl, $C_{6-10}$ monocyclic or bicyclic aryl, or $C_{6-10}$ monocyclic or bicyclic aryl($C_{1-6}$) alkyl;

$R^4$ is O, OH, CN, LG, or halogen, wherein LG is a suitable leaving group; and

represents a single or double bond.

In certain embodiments, the present invention provides a compound of formula II:

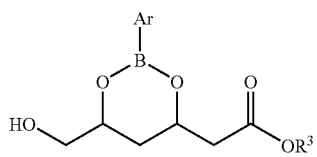

wherein:

Ar is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur; and $R^3$ is straight or branched $C_{1-8}$ alkyl, $C_{6-10}$ monocyclic or bicyclic aryl, or $C_{6-10}$ monocyclic or bicyclic aryl($C_{1-6}$) alkyl.

The present invention also provides a process for the manufacture of a compound of formula II:

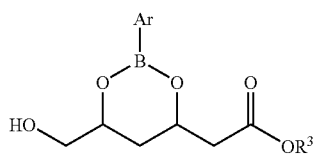

wherein:

Ar is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur; and $R^3$ is straight or branched $C_{1-8}$ alkyl, $C_{6-10}$ monocyclic or bicyclic aryl, or $C_{6-10}$ monocyclic or bicyclic aryl($C_{1-6}$) alkyl, which comprises the steps of:

(a) reacting a compound of formula III:

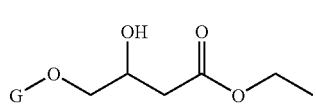

wherein:

G is a suitable hydroxyl protecting group, with the anion of a suitable acetate to give a compound of formula IV:

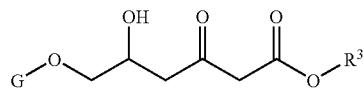

wherein:

G is a suitable hydroxyl protecting group; and $R^3$ is straight or branched $C_{1-8}$ alkyl, $C_{6-10}$ monocyclic or bicyclic aryl, or $C_{6-10}$ monocyclic or bicyclic aryl($C_{1-6}$)alkyl, (b) reducing said compound of formula IV to give a compound of formula V:

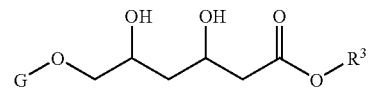

where:

G is a suitable hydroxyl protecting group; and $R^3$ is straight or branched $C_{1-8}$ alkyl, $C_{6-10}$ monocyclic or bicyclic aryl, or $C_{6-10}$ monocyclic or bicyclic aryl($C_{1-6}$)alkyl, (c) reacting the compound of formula V with $ArB(OH)_2$ to give a compound of formula VI:

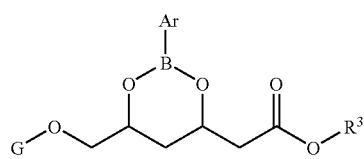

where:

G is a suitable hydroxyl protecting group; and $R^3$ is straight or branched $C_{1-8}$ alkyl, $C_{6-10}$ monocyclic or bicyclic aryl, or $C_{6-10}$ monocyclic or bicyclic aryl($C_{1-6}$)alkyl, and (d) deprotection of the compound of formula VI to give a compound of formula II.

Another embodiment of the present invention provides a compound of formula VI:

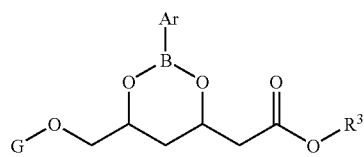

where:
G is a suitable hydroxyl protecting group; and
R³ is straight or branched $C_{1-8}$ alkyl, $C_{6-10}$ monocyclic or bicyclic aryl, or $C_{6-10}$ monocyclic or bicyclic aryl($C_{1-6}$)alkyl.

Suitable hydroxyl protecting groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference. In certain embodiments, the G moiety of a compound of any of formulae III, IV, V, and VI is selected from esters, ethers, silyl ethers, alkyl ethers, arylalkyl ethers, and alkoxyalkyl ethers. In other embodiments, the G moiety of a compound of any of formulae III, IV, V, and VI is tetrahydropyranyl, tert-butyldimethyl silyl, or trityl.

In certain embodiments, the Ar moiety of ArB(OH)₂ is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur. In other embodiments, the Ar moiety of ArB(OH)₂ is an optionally substituted phenyl or naphthyl ring. According to another embodiment, the Ar moiety of ArB(OH)₂ is an optionally substituted 5-10 membered monocyclic or bicyclic heteroaryl ring having 1-4 nitrogen atoms. In certain embodiments the Ar moiety of ArB(OH)₂ is quinolinyl. Examples of suitable substituents include $C_{1-4}$ straight or branched alkyl, $C_{1-4}$ straight or branched alkoxy, nitro, and halo. Such groups include methyl, methoxy, nitro, and fluoro.

As used herein, the phrase "suitable acetate" refers to an acetate compound such that the anion of which, when reacted with a compound of formula III, provides a compound of formula IV. Such acetate groups include those having the formula $R^3OC(O)CH_3$, wherein R³ is as defined above. In certain embodiments, said suitable acetate is tert-butyl acetate.

The reduction of a compound of formula V to a compound of formula VI is performed by various methods known to one of ordinary skill in the art. Such reduction methods include those describe in "Advanced Organic Chemistry," Jerry March, 4th Ed., pp. 351-357, John Wiley and Sons, N.Y. (1992). In certain embodiments, the reduction of a compound of formula V to a compound of formula VI is achieved using sodium borohydride.

The deprotection of a compound of formula VI to afford a compound of formula II is achieved using methods known to one of ordinary skill in the art. One of ordinary skill in the art would recognize that methods appropriate to achieve removal of the protecting group, "G", of compound VI depend upon the actual protecting group used and include those described by Greene. For example, when the hydroxyl protecting group of compound VI is a G is tetrahydropyranyl, tert-butyldimethyl silyl, or trityl group, such removal may be achieved by treatment with mild acid. In certain embodiments, the removal of the G group is achieved using trifluoroacetic acid.

In other embodiments, the compound of formula II:

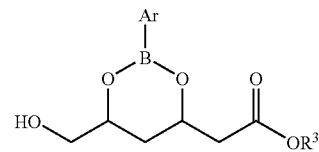

wherein:
Ar is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur; and
R³ is straight or branched $C_{1-8}$ alkyl, $C_{6-10}$ monocyclic or bicyclic aryl, or $C_{6-10}$ monocyclic or bicyclic aryl ($C_{1-6}$)alkyl, is oxidized to a compound of formula VIII:

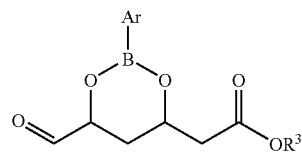

wherein:
Ar is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur; and
R³ is straight or branched $C_{1-8}$ alkyl, $C_{6-10}$ monocyclic or bicyclic aryl, or $C_{6-10}$ monocyclic or bicyclic aryl ($C_{1-6}$)alkyl.

The oxidation of a compound of formula II to a compound of formula VIII is achieved using various methods known to one of ordinary skill in the art. Such methods include those described in "Advanced Organic Chemistry," Jerry March, 4th Ed., pp. 351-357, John Wiley and Sons, N.Y. (1992). In certain embodiments, the oxidation of a compound of formula II to a compound of formula VIII is achieved using pyridinium chlorochromate or DMSO/oxalyl chloride. In other embodiments, the oxidation of a compound of formula II to a compound of formula VIII is achieved using DMSO/oxalyl chloride (also known as Swern oxidation).

Another embodiment of the present invention provides a compound of formula VIII:

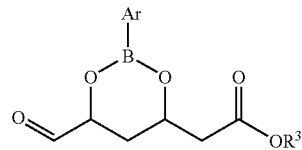

wherein:
Ar is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur; and $R^3$ is straight or branched $C_{1-8}$ alkyl, $C_{6-10}$ monocyclic or bicyclic aryl, or $C_{6-10}$ monocyclic or bicyclic aryl($C_{1-6}$)alkyl.

In yet other embodiments, a compound of formula II:

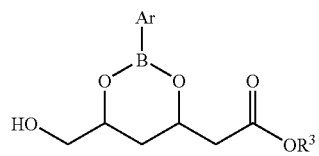

II wherein:

Ar is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur; and $R^3$ is straight or branched $C_{1-8}$ alkyl, $C_{6-10}$ monocyclic or bicyclic aryl, or $C_{6-10}$ monocyclic or bicyclic aryl ($C_{1-6}$)alkyl, is converted to a compound of formula IX:

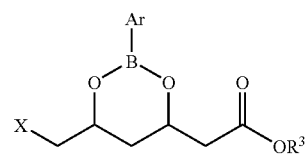

IX wherein:

Ar is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur;

$R^3$ is straight or branched $C_{1-8}$ alkyl, $C_{6-10}$ monocyclic or bicyclic aryl, or $C_{6-10}$ monocyclic or bicyclic aryl ($C_{1-6}$)alkyl; and X is a halogen.

The conversion of a compound of formula II to a compound of formula IX is achieved by halogenating methods known to one of skill in the art. For example, compounds of formula IX wherein X is Br are formed from a compound of formula II by reacting with aqueous HBr solution or by reaction with triphenylphosphine and $CBr_4$. One of skill in the art would recognize that compounds of formula IX where X is chloro, iodo, and fluoro may be prepared by analogous methods. Such methods include those described in "Advanced Organic Chemistry," Jerry March, $4^{th}$ Ed., pp. 351-357, John Wiley and Sons, N.Y. (1992).

Another embodiment of the present invention provides a compound of formula IX:

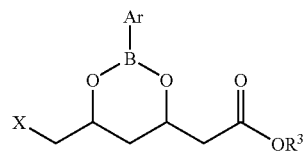

IX wherein:

Ar is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur;

$R^3$ is straight or branched $C_{1-8}$ alkyl, $C_{6-10}$ monocyclic or bicyclic aryl, or $C_{6-10}$ monocyclic or bicyclic aryl ($C_{1-6}$)alkyl; and X is a halogen.

In still other embodiments, a compound of formula IX:

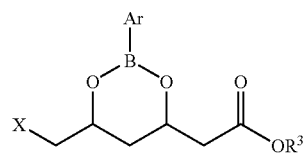

IX wherein:

Ar is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur;

$R^3$ is straight or branched $C_{1-8}$ alkyl, $C_{6-10}$ monocyclic or bicyclic aryl, or $C_{6-10}$ monocyclic or bicyclic aryl ($C_{1-6}$)alkyl; and X is a halogen, is converted to a compound of formula VII:

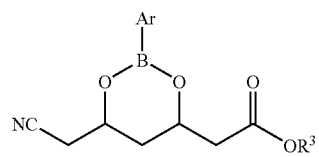

VII wherein:

Ar is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur; and $R^3$ is straight or branched $C_{1-8}$ alkyl, $C_{6-10}$ monocyclic or bicyclic aryl, or $C_{6-10}$ monocyclic or bicyclic aryl ($C_{1-6}$)alkyl.

Another embodiment of the present invention provides a compound of formula VII:

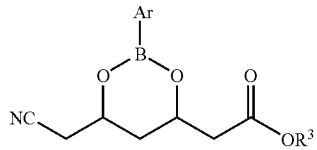

wherein:
Ar is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur; and $R^3$ is straight or branched $C_{1-8}$ alkyl, $C_{6-10}$ monocyclic or bicyclic aryl, or $C_{6-10}$ monocyclic or bicyclic aryl($C_{1-6}$)alkyl.

According to another embodiment, the Ar group of formula VII is other than phenyl when $R^3$ is t-butyl.

In certain embodiments, a compound of formula IIa is used in the synthesis of atorvastatin, cerivastatin, pitavastatin, fluvastatin or rosuvastatin. In other embodiments, a compound of formula II is used in the synthesis of atorvastatin, cerivastatin, pitavastatin, fluvastatin or rosuvastatin.

In certain embodiments, the hydroxyl moiety of formula II is converted into a suitable leaving group to form a compound of formula X:

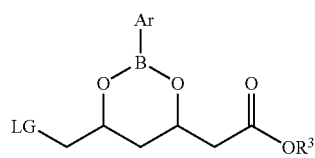

wherein:
Ar is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur;

$R^3$ is straight or branched $C_{1-8}$ alkyl, $C_{6-10}$ monocyclic or bicyclic aryl, or $C_{6-10}$ monocyclic or bicyclic aryl($C_{1-6}$)alkyl; and LG is a suitable leaving group.

Another embodiment of the present invention provides a compound of formula X:

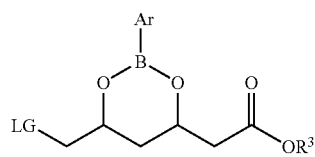

wherein:
Ar is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur;

$R^3$ is straight or branched $C_{1-8}$ alkyl, $C_{6-10}$ monocyclic or bicyclic aryl, or $C_{6-10}$ monocyclic or bicyclic aryl($C_{1-6}$)alkyl; and LG is a suitable leaving group.

As used herein, a suitable leaving group is a chemical moiety that is readily displaced by a desired incoming chemical moiety. Suitable leaving groups are well known in the art, e.g., see, "Advanced Organic Chemistry," Jerry March, 4$^{th}$ Ed., pp. 351-357, John Wiley and Sons, N.Y. (1992). Such leaving groups include, but are not limited to, halogen, alkoxy, sulphonyloxy, optionally substituted alkylsulphonyl, optionally substituted alkenylsulfonyl, optionally substituted arylsulfonyl, and diazonium moieties. Examples of suitable leaving groups include chloro, iodo, bromo, fluoro, methanesulfonyl (mesyl), tosyl, triflate, nitro-phenylsulfonyl (nosyl), and bromo-phenylsulfonyl (brosyl). In certain embodiments, the LG moiety of a compound of formula X is sulphonyloxy, optionally substituted alkylsulphonyl, optionally substituted alkenylsulfonyl, or optionally substituted arylsulfonyl. In other embodiments, the LG moiety of a compound of formula X is optionally substituted alkylsulphonyl. In yet other embodiments, the LG moiety of a compound of formula X is mesyl. According to another embodiment, the LG moiety of a compound of formula X is tosyl.

In other embodiments, the leaving group moiety LG of a compound of formula X is displaced with cyanide to afford a compound of formula VII:

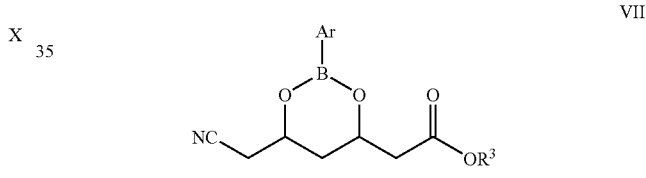

wherein:
Ar is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur; and $R^3$ is straight or branched $C_{1-8}$ alkyl, $C_{6-10}$ monocyclic or bicyclic aryl, or $C_{6-10}$ monocyclic or bicyclic aryl($C_{1-6}$)alkyl.

In still other embodiments, the present invention relates to optically active boronate derivatives of formula IIa which are useful intermediates for the synthesis of HMG-CoA enzyme inhibitors such as atorvastatin, cerivastatin, rosuvastatin, pitavastatin, fluvastatin, and the like. Accordingly, another aspect of the present invention relates to a compound of any of formulae IIa-1, IIa-2, IIa-3, and IIa-4:

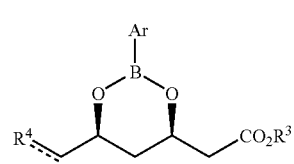

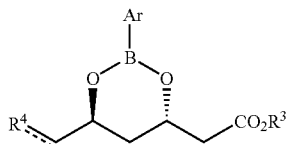
IIa-2

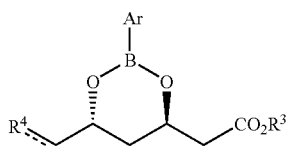
IIa-3

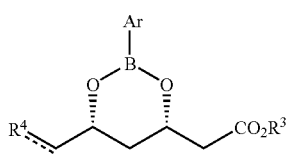
IIa-4 wherein each Ar, $R^3$, and $R^4$ is as defined above and described in various embodiments above and herein.

In certain embodiments, the present invention provides a compound of formula IIa-1:

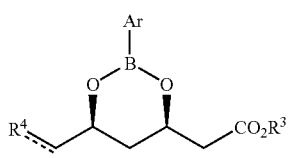
IIa-1 wherein Ar, $R^3$, and $R^4$ are as defined above and described in various embodiments above and herein.

According to another embodiment, the present invention provides a compound of any of formulae II-1, II-2, II-3, or II-4:

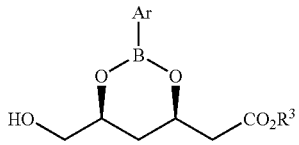
II-1

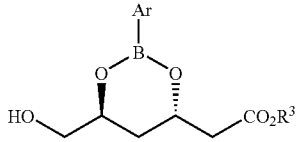
II-2

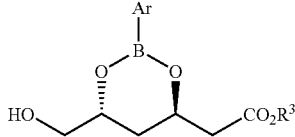
II-3

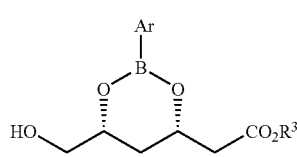
II-4 wherein each Ar and $R^3$ is as defined above and described in various embodiments above and herein.

Another aspect of the present invention relates to a compound of formula II-1:

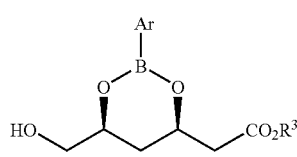
II-1 wherein Ar and $R^3$ are as defined above and described in various embodiments above and herein.

One of ordinary skill in the art would recognize that in the process for preparing a compound of formula IIa, as described herein, either stereoisomer of the compound of formula III:

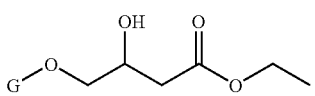
III may be utilized, wherein G is as defined above. Thus, either of a compound of formula III-1 or III-2:

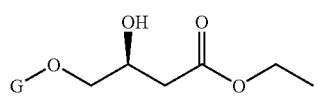
III-1

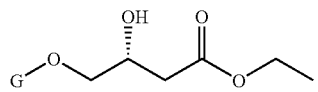
III-2 wherein each G is as defined above, may be used in said process to prepare a compound of any of formulae IIa-1, IIa-2, IIa-3, and IIa-4. Specifically, one of ordinary skill in the art would recognize that a compound of formula III-1 is useful for preparing compounds of formulae IIa-1 and IIa-2 whereas a compound of formula III-2 is useful for preparing compound of formulae IIa-3 and IIa-4.

Accordingly, another aspect of the present invention relates to a method for preparing a compound of formula IIb:

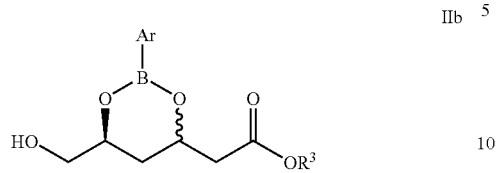
IIb wherein:
Ar is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur; and
$R^3$ is a straight or branched $C_{1-8}$ alkyl, $C_{6-10}$ monocyclic or bicyclic aryl, or $C_{6-10}$ monocyclic or bicyclic aryl($C_{1-6}$) alkyl, which comprises the steps of:
(a) reacting a compound of formula III-1:

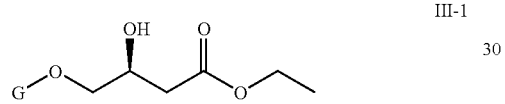
III-1 wherein:
G is a suitable hydroxyl protecting group, with the anion of a suitable acetate to give a compound of formula IV-1:

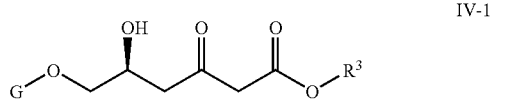
IV-1 wherein:
G is a suitable hydroxyl protecting group; and
$R^3$ is straight or branched $C_{1-8}$ alkyl, $C_{6-10}$ monocyclic or bicyclic aryl, or $C_{6-10}$ monocyclic or bicyclic aryl($C_{1-6}$)alkyl,
(b) reducing said compound of formula IV-1 to give a compound of formula V-1:

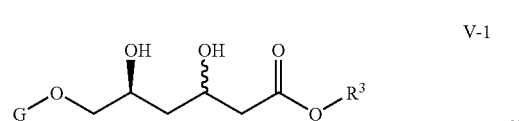
V-1 where:
G is a suitable hydroxyl protecting group; and
$R^3$ is straight or branched $C_{1-8}$ alkyl, $C_{6-10}$ monocyclic or bicyclic aryl, or $C_{6-10}$ monocyclic or bicyclic aryl($C_{1-6}$)alkyl, (c) reacting the compound of formula V-1 with $ArB(OH)_2$ to give a compound of formula VI-1:

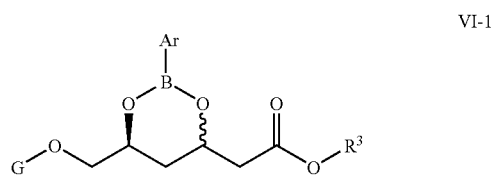
VI-1 where:
G is a suitable hydroxyl protecting group; and
$R^3$ is straight or branched $C_{1-8}$ alkyl, $C_{6-10}$ monocyclic or bicyclic aryl, or $C_{6-10}$ monocyclic or bicyclic aryl($C_{1-6}$)alkyl,
and
(d) deprotection of the compound of formula VI-1 to give a compound of formula IIb.

In certain embodiments, the reduction of a compound of formula IV-1 to a compound of formula V-1, or of a compound of formula IV-2 to a compound of formula V-2, occurs in a stereo-selective manner.

According to other embodiments, another aspect of the present invention relates to a method for preparing a compound of formula II-1:

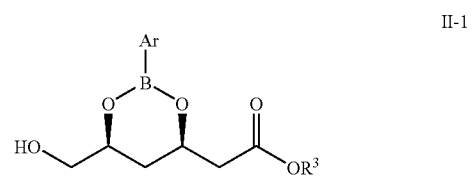
II-1 wherein:
Ar is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur; and
$R^3$ is a straight or branched $C_{1-8}$ alkyl, $C_{6-10}$ monocyclic or bicyclic aryl, or $C_{6-10}$ monocyclic or bicyclic aryl($C_{1-6}$) alkyl, which comprises the steps of:
(a) reacting a compound of formula III-1:

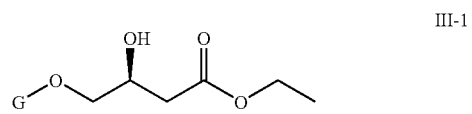
III-1 wherein:
G is a suitable hydroxyl protecting group, with the anion of a suitable acetate to give a compound of formula IV-1:

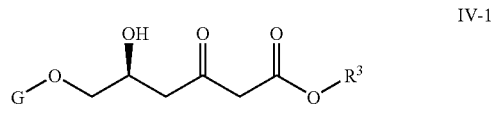
IV-1 wherein:
G is a suitable hydroxyl protecting group; and
R³ is straight or branched $C_{1-8}$ alkyl, $C_{6-10}$ monocyclic or bicyclic aryl, or $C_{6-10}$ monocyclic or bicyclic aryl($C_{1-6}$)alkyl, (b) reducing said compound of formula IV-1 to give a compound of formula V-3:

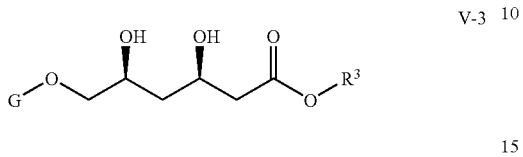

V-3 where:
G is a suitable hydroxyl protecting group; and
R³ is straight or branched $C_{1-8}$ alkyl, $C_{6-10}$ monocyclic or bicyclic aryl, or $C_{6-10}$ monocyclic or bicyclic aryl($C_{1-6}$)alkyl, (c) reacting the compound of formula V-3 with ArB(OH)₂ to give a compound of formula VI-3:

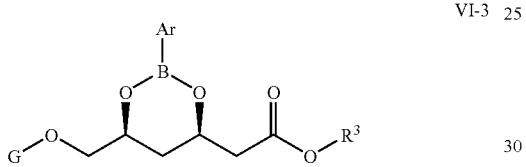

VI-3 where:
G is a suitable hydroxyl protecting group; and
R³ is straight or branched $C_{1-8}$ alkyl, $C_{6-10}$ monocyclic or bicyclic aryl, or $C_{6-10}$ monocyclic or bicyclic aryl($C_{1-6}$)alkyl,
and (d) deprotection of the compound of formula VI-3 to give a compound of formula II-1.

In other embodiments, the stereo-selective reduction of a compound of formula IV-1 to a compound of formula V-3 is performed in the presence of a borane reagent. In still other embodiments, said stereo-selective reduction is performed in the presence of methoxydiethylborane.

Yet another aspect of the present invention relates to a method for preparing a compound of formula IIc:

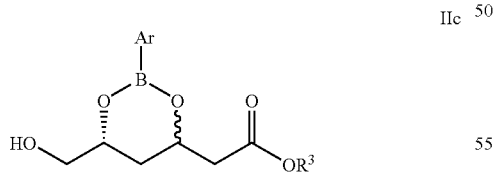

IIc wherein:
Ar is an unsubstituted or substituted ring selected from $C_{6-10}$ monocyclic or bicyclic aryl or a 5-10 membered monocyclic or bicyclic heteroaryl ring having 1-4 heteroatoms independently selected from nitrogen, oxygen, or sulfur; and
R³ is a straight or branched $C_{1-8}$ alkyl, $C_{6-10}$ monocyclic or bicyclic aryl, or $C_{6-10}$ monocyclic or bicyclic aryl($C_{1-6}$) alkyl, which comprises the steps of:
(a) reacting a compound of formula III-2:

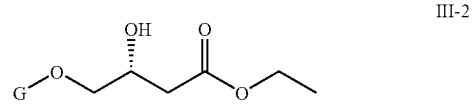

III-2 wherein:
G is a suitable hydroxyl protecting group, with the anion of a suitable acetate to give a compound of formula IV-2:

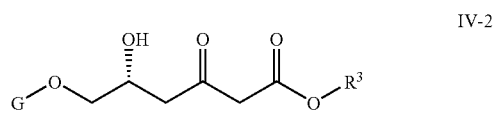

IV-2 wherein:
G is a suitable hydroxyl protecting group; and
R³ is straight or branched $C_{1-8}$ alkyl, $C_{6-10}$ monocyclic or bicyclic aryl, or $C_{6-10}$ monocyclic or bicyclic aryl($C_{1-6}$)alkyl, (b) reducing said compound of formula IV-2 to give a compound of formula V-2:

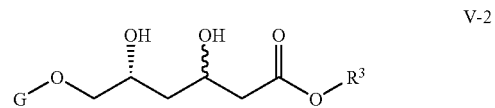

V-2 where:
G is a suitable hydroxyl protecting group; and
R³ is straight or branched $C_{1-8}$ alkyl, $C_{6-10}$ monocyclic or bicyclic aryl, or $C_{6-10}$ monocyclic or bicyclic aryl($C_{1-6}$)alkyl, (c) reacting the compound of formula V-2 with ArB(OH)₂ to give a compound of formula VI-2:

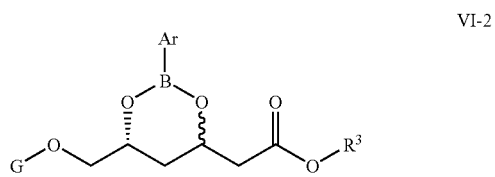

VI-2 where:
G is a suitable hydroxyl protecting group; and
R³ is straight or branched $C_{1-8}$ alkyl, $C_{6-10}$ monocyclic or bicyclic aryl, or $C_{6-10}$ monocyclic or bicyclic aryl($C_{1-6}$)alkyl,
and (d) deprotection of the compound of formula VI-2 to give a compound of formula IIc.

In certain embodiments, the present invention provides a compound of any of formulae VII-1, VII-2, VII-3, or VII-4:

VII-1
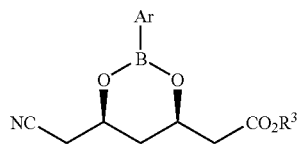

VII-2
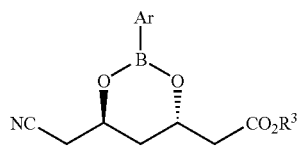

VII-3
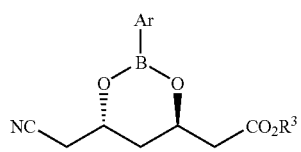

VII-4
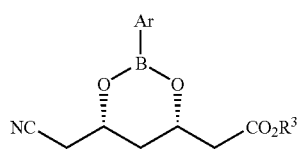

wherein each Ar and $R^3$ is as defined above and described in various embodiments above and herein.

Another aspect of the present invention relates to a compound of formula VII-1:

VII-1
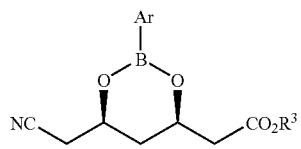

wherein Ar and $R^3$ are as defined above and described in various embodiments above and herein.

In other embodiments, the present invention provides a compound of any of formulae X-1, X-2, X-3, or X-4:

X-1
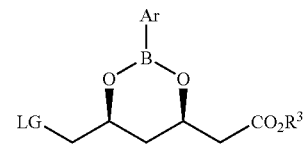

X-2
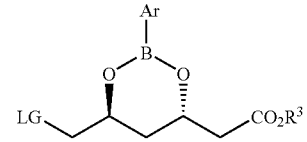

X-3
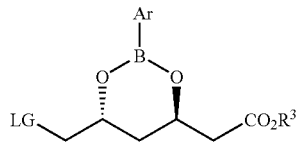

X-4
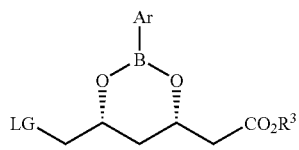

wherein each LG, Ar and $R^3$ is as defined above and described in various embodiments above and herein.

Another aspect of the present invention relates to a compound of formula X-1:

X-1
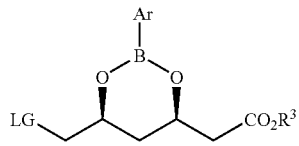

wherein Ar and $R^3$ are as defined above and described in various embodiments above and herein.

In still other embodiment, the present invention provides a compound of any of formulae IX-1, IX-2, IX-3, or IX-4:

IX-1
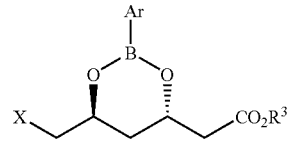

IX-2
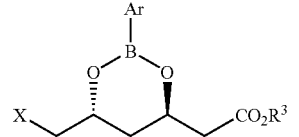

IX-3
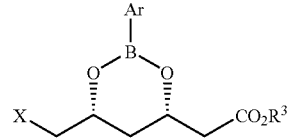

IX-4 wherein each X, Ar and $R^3$ is as defined above and described in various embodiments above and herein.

Another aspect of the present invention relates to a compound of formula IX-1:

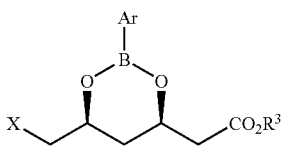

IX-1 wherein Ar and $R^3$ are as defined above and described in various embodiments above and herein.

Another aspect of the present invention provides a compound of any of formulae VIII-1, VIII-2, VIII-3, or VIII-4

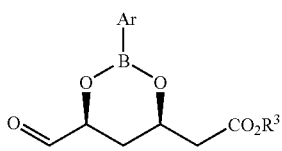

VIII-1

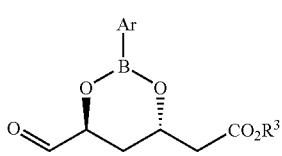

VIII-2

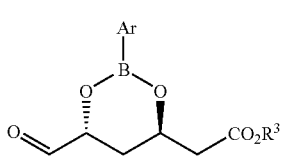

VIII-3

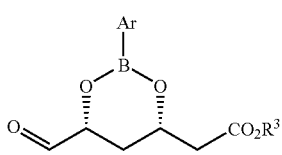

VIII-4 wherein each Ar and $R^3$ is as defined above and described in various embodiments above and herein.

Another aspect of the present invention relates to a compound of formula VIII-1:

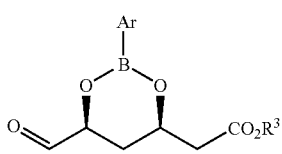

VIII-1 wherein Ar and $R^3$ are as defined above and described in various embodiments above and herein.

The invention is further illustrated with examples below, which are not intended to be limiting.

EXAMPLES

Example 1

Synthesis of Methyl 4-triphenylmethyloxy-3(S)-hydroxybutyrate

To 25 g of methyl 3(S), 4-dihydroxybutanoate was added 250 mL of DCM and stirred to dissolve. 19.8 g of pyridine was added and cooled to 0° C. 41.4 g of trityl chloride was dissolved in 50 mL of DMC and was added at 0-5° C. for 15 minutes. The temperature was allowed to rise to room temperature and was stirred at room temperature for 17 hours. Water was added and the layers were separated. The organic layer was washed with brine, dried and concentrated. The residue was triturated with 25 mL of cyclohexane and the product was purified to give 15 g of the pure product. $^1$H NMR (CDCl$_3$): 4.25 (m, 1H), 3.6 (s, 3H), 3.15 (d, 2H), 2.5 (m, 2H), 7.2-7.4 (m, 15H).

Example 2

Synthesis of Tert-butyl 6-triphenylmethyloxy-5(S)-hydroxy-3-oxohexanoate 125 mL of THF and 24 g of diisopropylamine were charged and cooled to −15° C. 168 mL of 1.2 N n-BuLi was added at −15 to −5° C. and was stirred for 30 minutes. 21.56 g of tert-butyl acetate in 45 mL of THF, which was precooled to −45° C., was added maintaining the temperature between −45 to −25° C. for 60 minutes. The reaction mixture was cooled to −45° C. and 30 g of methyl 4-triphenylmethyloxy-3(S)-hydroxybutyrate in THF was added over a period of 20 minutes and the stirring was continued at −25° C. for 90 minutes. Water was added and the layers were separated. The aqueous layer was extracted using EtOAc and the combined organic layers were washed with brine, water, dried and concentrated to give the title compound which was used as such for the next step.

Example 3

Synthesis of Tert-butyl 6-triphenylmethyloxy-3(R),5(S)-dihydroxyhexanoate

To the crude tert-butyl 6-triphenylmethyloxy-5(S)-hydroxy-3-oxohexanoate was added 150 mL of THF followed by 15 mL of MeOH and was chilled to −60° C. 26 mL of methoxydiethylborane (50% solution in THF) was added over a period of 20 minutes and stirring was continued for a further 30 minutes. The reaction mixture was cooled to −80° C. and 5 g of sodium borohydride was added in portions and the after completion of addition the reaction mixture was stirred for 5 hours at −78° C. Acetic acid was added to adjust the pH to 7 and water was added. The aqueous layer was extracted using EtOAC, washed with brine, dried and concentrated to give the title compound which was used as such for the next step.

Example 4

Synthesis of Tert-butyl-6-triphenylmethyloxy-3(R),5 (S)-phenylboranatohexanoate

The crude tert-butyl 6-triphenylmethyloxy-3(R),5(S)-dihydroxyhexanoate was dissolved in 100 mL of toluene and 5.6 g of phenyl boronic acid was added. Water was removed by azeotropic distillation over a period of 3 hours. The reaction mixture was cooled to room temperature and toluene was removed under reduced pressure. 30 mL of methanol was added and the precipitated solid was filtered to give 10 g of the title product.

Example 5

Synthesis of Tert-butyl-6-hydroxy-3(R),5(S)-phenylboranatohexanoate

To 5 g of tert-butyl-6-triphenylmethyloxy-3(R),5(S)-phenylboranatohexanoate was added 20 mL of DCM and was chilled to 0° C. 5 mL of TFA was added and was stirred at 20° C. for 6 hours. Water was separated and the organic layer was washed with bicarbonate, brine, dried and concentrated to give the title product, which was purified by column chromatography. $^1$H NMR (CDCl$_3$): 7.7-7.8 (m, 2H), 7.4-7.5 (m, 1H), 7.3-7.4 (m, 2H), 4.5 (m, 1H), 4.2 (m, 1H), 3.6 (m, 1H), 3.5 (m, 1H), 2.55 (m, 1H), 2.45 (m, 1H), 2.0 (m, 1H), 1. 7 (m, 1H) 1.5 (s, 9H)

Example 6

Synthesis of Tert-butyl-6-cyano-3(R),5(R)-phenylboranatohexanoate 5 g of tert-butyl-6-hydroxy-3(R),5(S)-phenylboranatohexanoate was taken in dichloromethane (50 mL) and pyridine (10 mL) was added. The contents were cooled to −10° C. and methanesulfonyl chloride (1 equivalent) was added drop wise. After 5-6 hours of stirring at 0° C., the contents were washed with bicarbonate, water and brine. The solvent was removed under reduced pressure to afford the O-methanesulfonyl derivative, which was used as such for the next step. The crude mesylate was taken in DMSO (5 vols.) and 1.5 equivalents of potassium cyanide was added. The contents were maintained at reflux for a period of 18-22 hours. DMSO was removed under reduced pressure and the contents were extracted using ethyl acetate and was washed with bisulfite, brine and solvent was removed under reduced pressure to afford the desired product.

Example 7

Synthesis of Tert-butyl-6-oxo-3(R),5(S)-phenylboranatohexanoate 4.3 g of dimethylsulfoxide was added drop wise to a solution of 2.4 mL of oxalyl chloride in 100 mL of dichloromethane and the mixture maintained at −78° C. The mixture was stirred at that temperature for a period of 15 minutes and a solution of 5 g of tert-butyl-6-hydroxy-3(R), 5(S)-phenylboranatohexanoate dissolved in dichloromethane was added drop wise. After stirring for 15 minutes, 17 mL of triethyl amine was added and the reaction mixture was allowed to warm to ambient temperature over a 2 hour period. The reaction mixture was concentrated and the residue was dissolved in water and extracted using diethyl ether. Removal of solvent afforded the title compound.

Example 8

Synthesis of Tert-butyl-6-triphenylmethyloxy-3(R),5(S)(1-napththalenyl)boranatohexanoate The crude tert-butyl 6-triphenylmethyloxy-3(R),5(S)-dihydroxyhexanoate was dissolved in 100 mL of toluene and 7.1 g of 1-naphthalene boronic acid was added. Water was removed by azeotropic distillation over a period of 3 hours. The reaction mixture was cooled to room temperature and toluene was removed under reduced pressure. 30 mL of methanol was added and the precipitated solid was filtered to give 14 g of the title product.

Example 9

Synthesis of Tert-butyl 6-triphenylmethyloxy-3(R),5(S)-(2-methylphenyl)boranatohexanoate The crude tert-butyl 6-triphenylmethyloxy-3(R),5(S)-dihydroxyhexanoate was dissolved in 100 mL of toluene and 6.1 g of 2-methylphenyl boronic acid was added. Water was removed by azeotropic distillation over a period of 3 hours. The reaction mixture was cooled to room temperature and toluene was removed under reduced pressure. 30 mL of methanol was added and the precipitated solid was filtered to give 12 g of the title product:

Example 10

Synthesis of Tert-butyl 6-triphenylmethyloxy-3(R),5(S)-(4-methoxyphenyl)boranatohexanoate The crude tert-butyl 6-triphenylmethyloxy-3(R),5(S)-dihydroxyhexanoate was dissolved in 100 mL of toluene and 6.3 g of 4-methoxyphenyl boronic acid was added. Water was removed by azeotropic distillation over a period of 3 hours. The reaction mixture was cooled to room temperature and toluene was removed under reduced pressure. 30 mL of methanol was added and the precipitated solid was filtered to give 12 g of the title product.

Example 11

Synthesis of Tert-butyl 6-triphenylmethyloxy-3(R),5(S)-(8-quinolinyl)boranatohexanoate The crude tert-butyl 6-triphenylmethyloxy-3(R),5(S)-dihydroxyhexanoate was dissolved in 100 mL of toluene and 6.1 g of quinoline-8-boronic acid was added. Water was removed by azeotropic distillation over a period of 3 hours. The reaction mixture was cooled to room temperature and toluene was removed under reduced pressure. 30 mL of methanol was added and the precipitated solid was filtered to give 11 g of the title product.

Example 12

Synthesis of Tert-butyl-6-triphenylmethyloxy-3(R),5(S)-(3-nitrophenyl)boranatohexanoate The crude tert-butyl 6-triphenylmethyloxy-3(R),5(S)-dihydroxyhexanoate was dissolved in 100 mL of toluene and 6.1 g of 3-nitrophenyl boronic acid was added. Water was removed by azeotropic distillation over a period of 3 hours. The reaction mixture was cooled to room temperature and toluene was removed under reduced pressure. 30 mL of methanol was added and the precipitated solid was filtered to give 10 g of the title product.

Example 13

Synthesis of Tert-butyl-6-triphenylmethyloxy-3(R),5(S)-(2,6-difluorophenyl)boranatohexanoate The crude tert-butyl 6-triphenylmethyloxy-3(R),5(S)-dihydroxyhexanoate was dissolved in 100 mL of toluene and 6.3 g of 2,6-difluorophenyl boronic acid was added. Water was removed by azeotropic distillation over a period of 3 hours. The reaction mixture was cooled to room temperature and toluene was removed under reduced pressure. 30 mL of methanol was added and the precipitated solid was filtered to give 12 g of the title product.

Representative formulae of the present invention are set forth in Table 1, below.

TABLE 1

Representative Formulae of the Present Invention

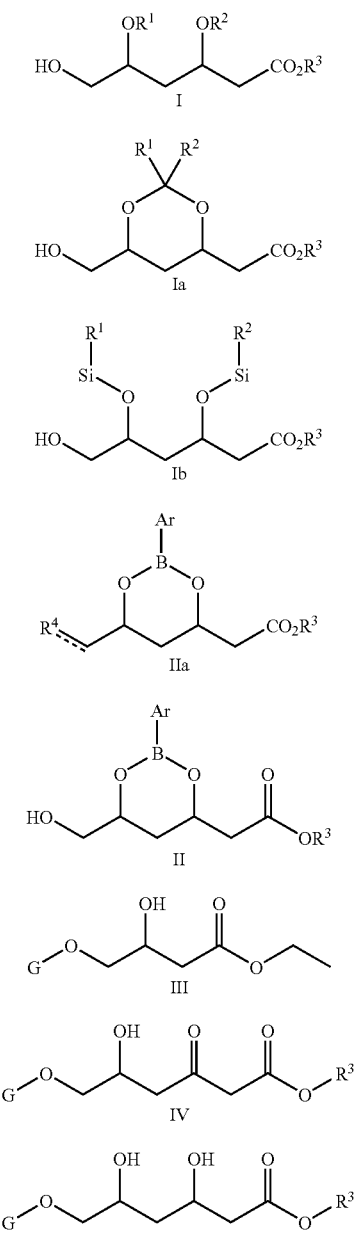

TABLE 1-continued

Representative Formulae of the Present Invention

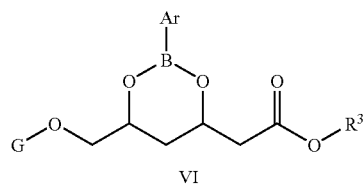

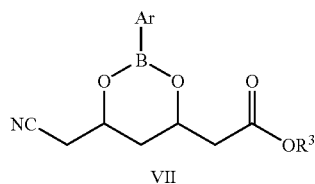

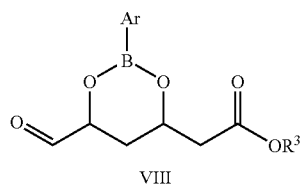

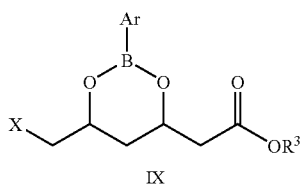

wherein all variables are as defined above and herein.

Representative compounds of the present invention are set forth in Table 2, below.

TABLE 2

Representative Compounds of the Present Invention

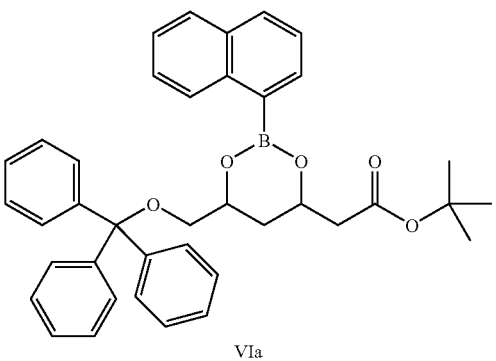

TABLE 2-continued
Representative Compounds of the Present Invention
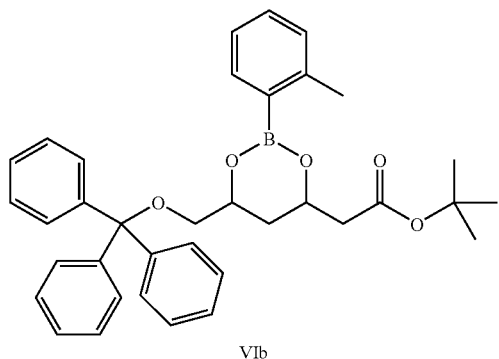
VIb
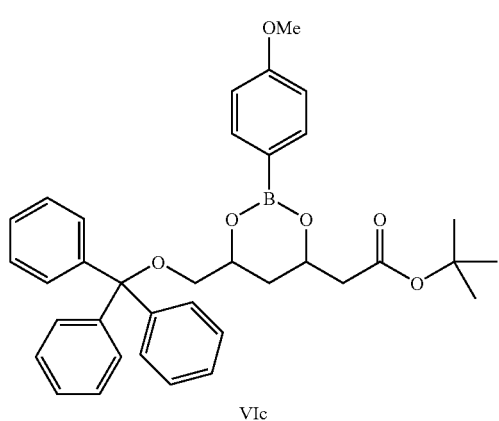
VIc
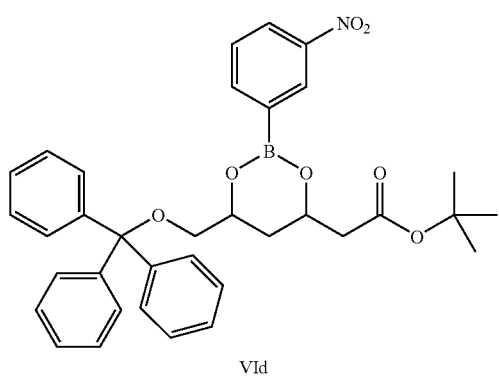
VId
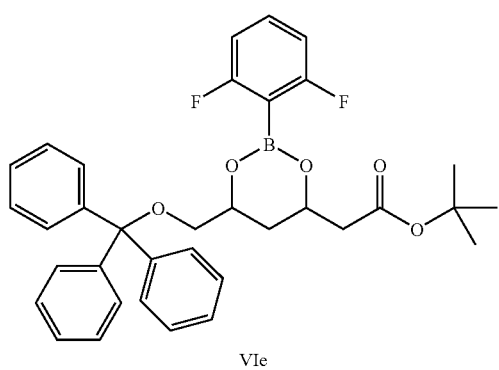
VIe
TABLE 2-continued
Representative Compounds of the Present Invention
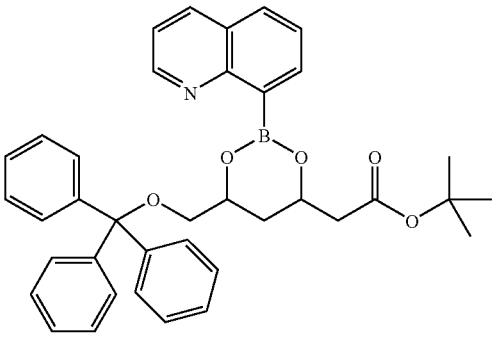
VIf
Compounds of the present invention are prepared according to Schemes 1-7, as shown below, by methods described in the Examples, and by methods known in the art.
Scheme 1:
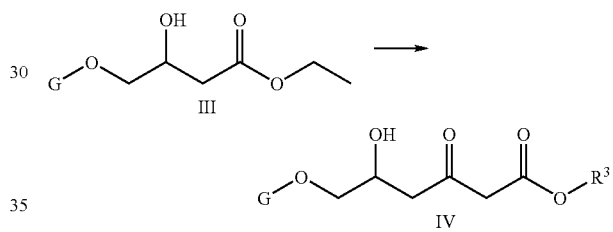
Scheme 2:
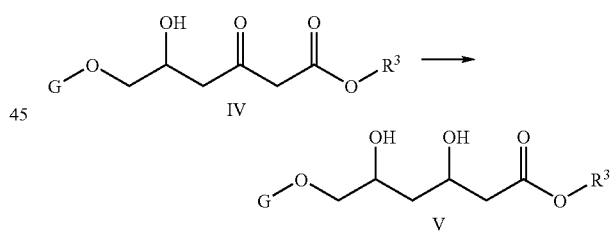
Scheme 3:
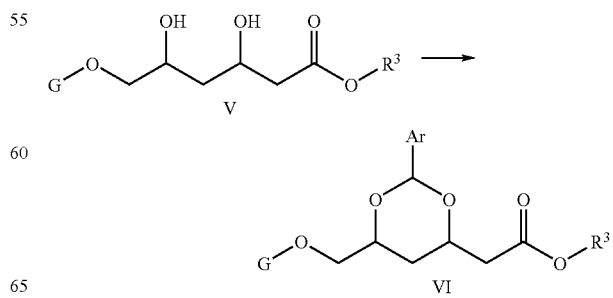

Scheme 4:
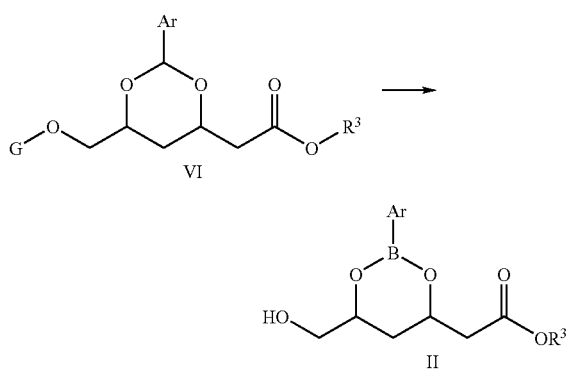
Scheme 5:
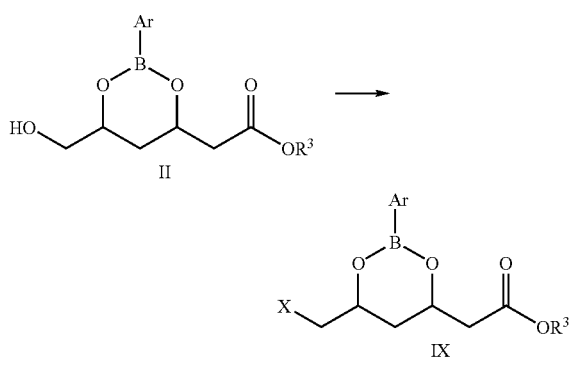
Scheme 6:
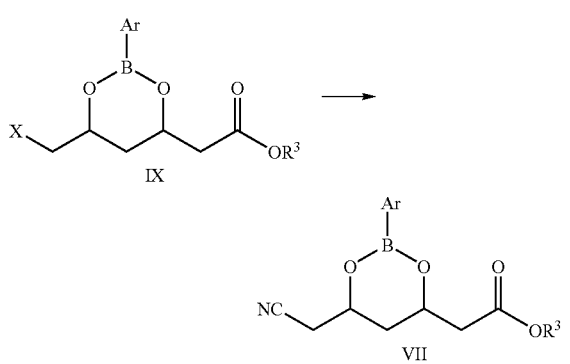
Scheme 7:
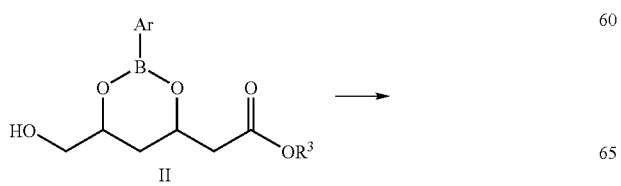
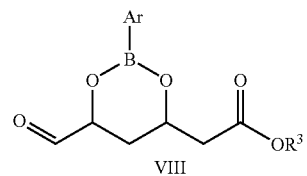
We claim:
1. A compound of formula IIa:
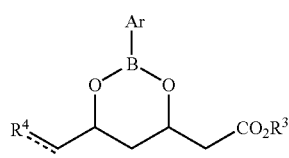
wherein:
Ar is an unsubstituted or substituted phenyl ring;
$R^3$ is t-butyl;
$R^4$ is O, OH, CN, LG, or halogen, wherein LG is a suitable leaving group; and
⇌ represents a single or double bond.
2. The compound according to claim 1, wherein said compound is selected from the following formulae IIa-1, IIa-2, IIa-3, or IIa-4:
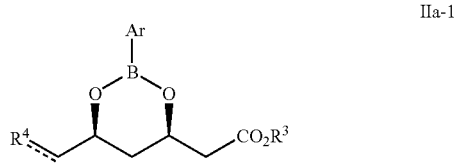
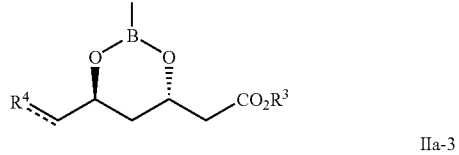
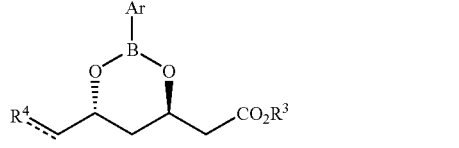

3. The compound according to claim 2, wherein said compound is of formula IIa-1:

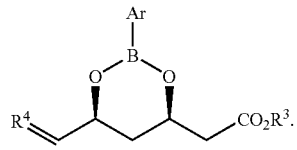

IIa-1

4. The compound according to claim 1, wherein said compound is a compound of formula II:

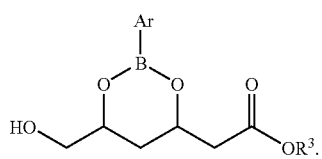

II

5. The compound according to claim 4, wherein said compound is selected from the following formulae II-1, II-2, II-3, or II-4:

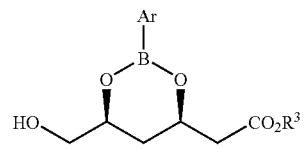

II-1

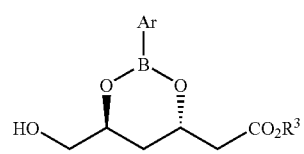

II-2

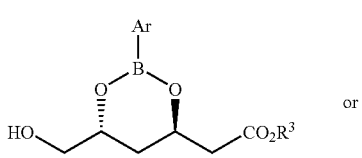

II-3 or

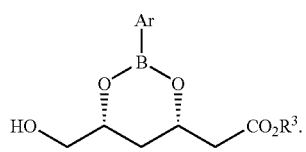

II-4

6. The compound according to claim 5, wherein said compound is of formula II-1:

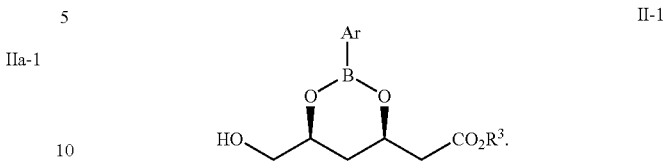

II-1

7. The compound according to claim 1, wherein said compound is of formula VI:

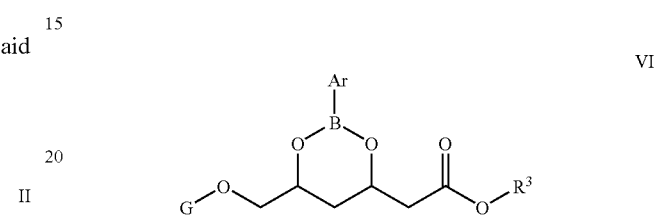

VI wherein G is a suitable hydroxyl protecting group.

8. The compound according to claim 1, wherein said compound is of formula VIII:

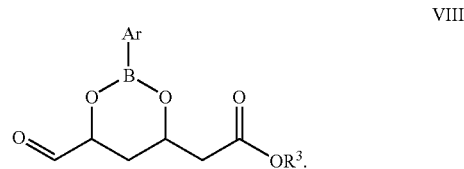

VIII

9. The compound according to claim 1, wherein said compound is of formula IX:

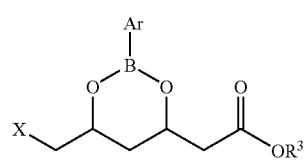

IX wherein X is a halogen.

10. The compound according to claim 1, wherein said compound is of formula X:

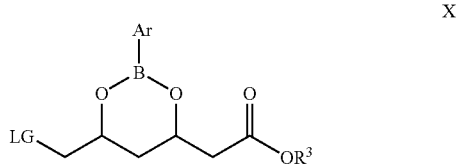

X wherein LG is a suitable leaving group.

11. The compound according to claim 1, used in the synthesis of atorvastatin, cerivastatin, pitavastatin, fluvastatin or rosuvastatin.

* * * * *